(12) United States Patent
Dahlstrom

(10) Patent No.: US 8,669,269 B2
(45) Date of Patent: Mar. 11, 2014

(54) IMIDAZOPYRIDINE DERIVATIVES WHICH INHIBIT THE SECRETION OF GASTRIC ACID

(76) Inventor: Mikael Dahlstrom, Bromarv (FI)

(*) Notice: Subject to any disclaimer, the term of this patent is extended or adjusted under 35 U.S.C. 154(b) by 173 days.

(21) Appl. No.: 13/132,564

(22) PCT Filed: Oct. 27, 2009

(86) PCT No.: PCT/FI2009/050861
§ 371 (c)(1),
(2), (4) Date: Jun. 2, 2011

(87) PCT Pub. No.: WO2010/063876
PCT Pub. Date: Jun. 10, 2010

(65) Prior Publication Data
US 2011/0237619 A1   Sep. 29, 2011

(30) Foreign Application Priority Data
Dec. 3, 2008 (FI) ................................. 20086158

(51) Int. Cl.
*A01N 43/42* (2006.01)
*A61K 31/44* (2006.01)
*C07D 491/02* (2006.01)
*C07D 498/02* (2006.01)

(52) U.S. Cl.
USPC ......................................... 514/300; 546/121

(58) Field of Classification Search
USPC .......................................... 514/300; 546/121
See application file for complete search history.

(56) References Cited

U.S. PATENT DOCUMENTS

| 4,450,164 | A | 5/1984 | Bristol et al. | |
| 4,725,601 | A | 2/1988 | Ueda et al. | |
| 6,313,136 | B1 * | 11/2001 | Amin et al. | 514/300 |

FOREIGN PATENT DOCUMENTS

| EP | 0033094 | A1 | 8/1981 |
| EP | 0204285 | A1 | 12/1986 |
| WO | 9955705 | A1 | 11/1999 |
| WO | 9955706 | A1 | 11/1999 |
| WO | 0220523 | A1 | 3/2002 |
| WO | 03018582 | A1 | 3/2003 |
| WO | 2004113338 | A1 | 12/2004 |
| WO | 2004113340 | A1 | 12/2004 |
| WO | 2005041961 | A1 | 5/2005 |
| WO | 2005058895 | A1 | 6/2005 |
| WO | 2006100119 | A1 | 9/2006 |
| WO | 2007039464 | A1 | 4/2007 |

OTHER PUBLICATIONS

International Search Report for PCT/FI2009/050861, Completed by the European Patent Office on Jan. 15, 2010, 4 Pages.
Kaminski et al. "Antiulcer Agents. 1. Gastric Antisecretory and Cytoprotective Properties of Substituted Imidazo[1,2-a] pyridines", Journal of Medicinal Chemistry 1985, vol. 28, p. 876-892.
Kaminski et al. "Antiulcer Agents . 5. Inhibition of Gastric H+/K+-ATPase by Substituted Imidazo[1,2-a]pyridines and Related Analogues and Its Implication in Modeling the High Affinity Potassium Ion Binding Site of the Gastric Proton Pump Enzyme", Journal of Medicinal Chemistry 1991, vol. 34, p. 533-541.
Sachs et al. "The Pharmacology of the Gastric Acid Pump: The H+,K+ ATPase1,2", Annu. Rev. Pharmacol. Toxicol. 1995, vol. 35, p. 277-305.

* cited by examiner

*Primary Examiner* — Niloofar Rahmani
(74) *Attorney, Agent, or Firm* — Brooks Kushman P.C.

(57) ABSTRACT

The present invention relates to substituted imidazo[1,2-a] pyridines of formula I where R is —CH$_2$COOH or —COOH, which inhibits exogenously or endogenously stimulated gastric acid secretion and can be used in the prevention and treatment of gastric acid related diseases and gastrointestinal inflammatory diseases.

10 Claims, No Drawings

IMIDAZOPYRIDINE DERIVATIVES WHICH INHIBIT THE SECRETION OF GASTRIC ACID

CROSS-REFERENCE TO RELATED APPLICATION

This application is the U.S. national phase of PCT Appln. No. PCT/FI2009/050861 filed Oct. 27, 2009 which claims priority to Finland application 20086158 filed Dec. 3, 2008, the disclosures of which are incorporated in their entirety by reference herein.

TECHNICAL FIELD

The present invention relates to novel imidazopyridine derivatives and pharmaceutically acceptable salts thereof, which inhibit exogenously or endogenously stimulated gastric acid secretion. Said compounds are useful in the prevention and treatment of gastrointestinal inflammatory diseases. In further aspects, the invention particularly relates to substituted imidazo[1,2-a]pyridines and pharmaceutically acceptable salts thereof, to processes for the preparation thereof, to pharmaceutical compositions containing said compounds as active ingredients, and to the use of said compounds in the manufacture of medicaments for the medical use indicated above.

STATE OF THE ART

Substituted imidazo[1,2-a]pyridines, useful in the treatment of peptic ulcer diseases, are known from EP0033094, U.S. Pat. No. 4,450,164, EP0204285, U.S. Pat. No. 4,725,601, WO99/55706, WO99/55705, WO03/018582 and WO2006/100119, and from publications by J. J. Kaminski et al. in the Journal of Medicinal Chemistry vol. 28, 876-892, 1985 and vol. 34, 533-541, 1991.

A review of the pharmacology of the gastric acid pump (the $H^+,K^+$-ATPase) is presented by Sachs et al. in Ann. Rev. Pharmacol. Toxicol. vol. 35, 277-305, 1995.

SUMMARY OF THE INVENTION

New substituted imidazo[1,2-a]pyridines have now been found, useful in the treatment of gastrointestinal inflammatory diseases, particularly in the treatment of peptic ulcer diseases. Said substituted imidazo[1,2-a]pyridines exhibit several advantageous properties, such as fast onset, high in vivo potency and/or long duration of action, high solubility and high dissolution rate. Due to their zwitterionic character these compounds form soluble salts both in acidic and alkaline solutions.

DISCLOSURE OF THE INVENTION

It has surprisingly been found that new substituted imidazo[1,2-a]pyridines of the general formula I are particularly effective as inhibitors of gastric acid secretion. Particularly, the present invention relates to substituted imidazo[1,2-a]pyridines of the general formula I where the substituent R is —$CH_2COOH$ or —COOH, and pharmaceutically acceptable salts thereof.

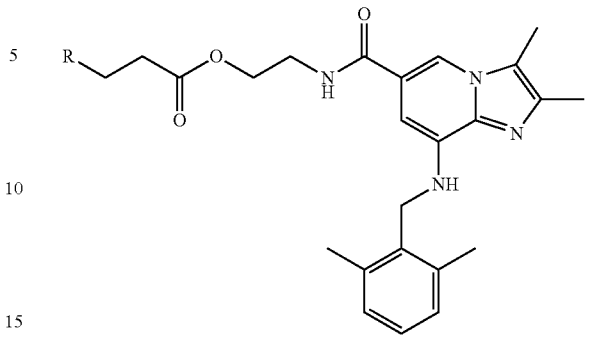

I

Depending on the process conditions the substituted imidazo[1,2-a]pyridines according to formula I are obtained either in neutral or in salt forms. Both the neutral forms and the salt forms of these compounds are within the scope of the present invention.

Process

The present invention also provides a process for the manufacture of the substituted imidazo[1,2-a]pyridines of formula I.

The process for manufacture of the substituted imidazo[1,2-a]pyridines of formula I is described in detail in the following.

The starting material 2,3-dimethyl-8-(2,6-dimethylbenzylamino)-N-hydroxyethyl-imidazo-[1,2-a]pyridine-6-carboxamide of formula II is obtainable using any suitable method known in the art, for example according to the process disclosed in WO02/20523, where a) Commercially available 6-chloro-5-nitronicotinoyl chloride of formula III

III is allowed to react with an alcohol of formula $R^1$—OH wherein $R^1$ is an alkyl group such as methyl, ethyl, isopropyl etc. to give the corresponding ester of following formula IV.

IV

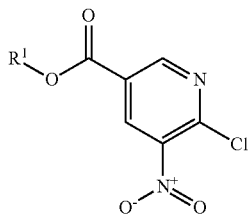

The reaction is typically carried out at standard conditions.
b) The compound of formula IV is allowed to react with ammonia to give the following compound of formula V

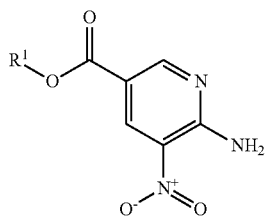

V where R¹ is an alkyl group such as methyl, ethyl, isopropyl etc. The reaction is typically carried out at standard conditions.

c) The compound of formula V is hydrogenated e.g. by using hydrogen gas and a hydrogenation catalyst such as Pd/C to give a compound of formula VI

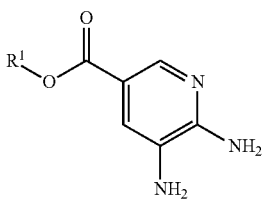

VI where R¹ is an alkyl group such as methyl, ethyl, isopropyl etc. The reaction is typically carried out at standard conditions in an inert solvent.

d) Imidazo[1,2]pyridine compound of formula VII where R¹ is an alkyl group such as methyl, ethyl, isopropyl etc. is prepared by allowing the compound of formula VI to react with 3-chloro-2-butanone or 3-bromo-2-butanone under standard conditions in an inert solvent such as acetone, acetonitrile, cyclohexanone and dimethylformamide etc. optionally in the presence of a base.

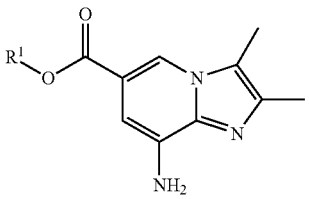

VII e) The imidazo[1,2]pyridine compound of formula VII is then allowed to react with a compound of formula VIII

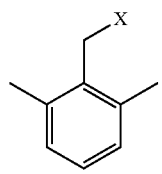

VIII where X is bromo (Br) or chloro (Cl) to give compound of formula IX wherein R¹ is an alkyl group such as methyl, ethyl, isopropyl etc. This reaction is typically carried out in an inert solvent such as acetone, acetonitrile, dimethoxyethane, ethanol or dimethylformamide optionally in the presence of a base, such as potassium carbonate, sodium carbonate or an organic amine, such as triethylamine.

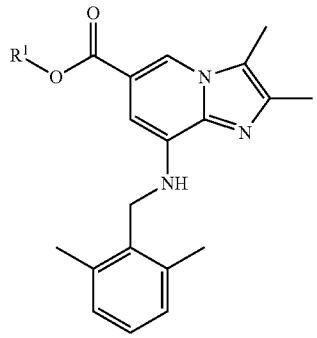

IX f) The compound of formula IX is allowed to react with ethanolamine to give the starting material 2,3-dimethyl-8-(2,6-dimethylbenzylamino)-N-hydroxyethyl-imidazo[1,2-a]pyridine-6-carboxamide of formula II. The reaction is typically carried out by heating the reactants in neat ethanolamine or in a solvent(s) such as methanol or ethanol at elevated temperature, such as from 40 to 80° C. The reaction is catalysed by cyanide salts and strong bases, such as sodium methoxide, potassium ethoxide and 1,8-diacabicyclo(5.4.0)undec-7-ene (DBU).

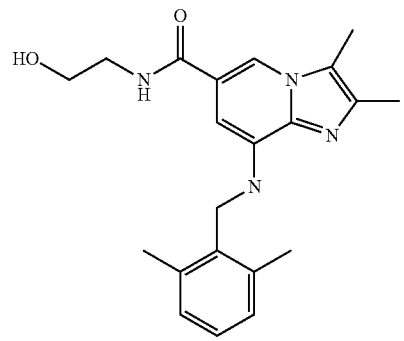

II

The process according to the invention for manufacture of the substituted imidazo[1,2-a]pyridines of formula I wherein R is —CH₂COOH or —COOH, comprises the following steps where the starting material 2,3-dimethyl-8-(2,6-dimethylbenzylamino)-N-hydroxyethyl-imidazo[1,2-a]pyridine-6-carboxamide, is allowed to react with 1-4 eq. of an anhydride selected from glutaric anhydride and succinic anhydride to give the desired compound of formula I. The reaction is carried out at an elevated temperature by heating the reactants in an inert solvent or a mixture thereof. Suitable inert solvents are for example DMF (dimethylformamide), DMA (dimethylacetamide), NMP (N-methylpyrrolidone), THF (tetrahydrofurane), cyclic ketones such as cyclohexanone and alicyclic ketones such as acetone and methylethyl ketone. Suitable reaction temperature ranges between 40 and 130° C., preferably between 60 to 120° C. The pressure may range from atmospheric pressure to $5 \times 10^2$ KPa. After the reaction the product is isolated for example using crystallization from the reaction mixture or precipitated using a suitable solvent, such as acetone.

Depending on the process conditions the substituted imidazo[1,2-a]pyridines according to formula I are obtained either in neutral or salt forms. Because of the zwitterionic nature, the compound of formula I is in the form of positively charged cation at pH≤4, such as hydrochloride salt, at pH≥8 it is in the form of negatively charged anion, such as carboxylate anion, whilst at pH ranging approx. between 5 and 7 the neutral form of the compound may exist because the dielectric point of the compound can be found around the pH range of 5-7.

In the preparation of salts of the substituted imidazo[1,2-a]pyridines of formula I, particularly acid addition salts, preferably acids capable of forming pharmaceutically acceptable salts are used. Examples of suitable acids are hydrochloric acid, sulphuric acid, phosphoric acid, nitric acid and sulphonic acids, such as methanesulphonic acid, ethanesulfonic acid, hydroxyethanesulphonic acid, toluenesulphonic acid and naphtalenesulphonic acid.

In the preparation of alkaline salts, such as sodium, potassium calcium and magnesium salts, preferably bases capable of forming pharmaceutically acceptable salts are used. These salts may be prepared by using bases such as sodium hydroxide, sodium carbonate, sodium bicarbonate, potassium hydroxide, potassium carbonate, potassium bicarbonate, calcium hydroxide, calcium acetate, magnesium hydroxide and magnesium acetate.

Medical Use

In a further aspect, the invention relates to the use of the substituted imidazo[1,2-a]pyridines of formula I in therapy. In particular, the invention provides the use of the substituted imidazo[1,2-a]pyridines of formula I in the manufacture of a medicament for the inhibition of gastric acid secretion and for the treatment of gastrointestinal inflammatory diseases, particularly peptic ulcer diseases.

It was revealed that the substituted imidazo[1,2-a]pyridines according to the invention have significant therapeutic effect. In rat studies, where the rats were administered 1 μmol/kg of the compounds according to the invention, a maximal inhibition of acid secretion of 100% was observed for Example 1 and 70% for Example 2. Thus these compounds may be used for the prevention and treatment of gastrointestinal inflammatory diseases and gastric acid related diseases, such as gastritis, reflux esophagitis, Zollinger-Ellison syndrome and peptic ulcer disease including gastric ulcer and duodenal ulcer in mammals including man. Furthermore, the compounds may be used for the treatment of other gastrointestinal disorders where gastric antisecretory effect is desirable, e.g. in patients with gastrinomas and in patients with acute upper gastrointestinal bleeding. The compounds may also be used for effective control and treatment of heartburn and other gastroesophageal reflux disease (GERD) symptoms, regurgitation, short and long-term management of acid reflux disease and nausea. They may also be used in patients in intensive care situations and pre- and postoperatively to prevent acid aspiration and stress ulceration.

The zwitterionic character gives the compounds of invention particularly favourable physical properties. These properties make the compounds suitable for different pharmaceutical compositions. The compounds according to the invention have good solubility in acidic media (e.g. in the stomach), which is beneficial for an instant release (IR) formulation. At neutral pH the compounds according to the invention e.g. the zwitterions have low solubility, which can be utilized in an extended release (ER) formulation. At basic pH the compounds according to the invention are in anionic forms, which have good solubility and are especially suitable for i.v. formulations.

After in vivo administration the compounds according to the invention generate linaprazan as the major metabolite. Linaprazan is a known inhibitor of gastric acid secretion. Thus the compounds of the invention also act as prodrugs for linaprazan.

Typical daily dose of the compounds according to the invention, as pharmaceutically active substances, varies within a wide range and will depend on various factors such as for example the individual requirement of each patient, the route of administration and the disease to be treated. In general, oral and parenteral dosages will be in the range of 5 to 500 mg per day of active substance, preferably in the range of 10 to 60 mg, for example 40 mg.

The compounds of the invention may be administered to the patient in a continuous treatment as well as on-demand treatment, depending on the individual requirements and disease. By the compounds of the invention possibilities to improve the quality of life for the individuals suffering from gastric acid related diseases and/or gastrointestinal inflammatory diseases are given.

The compounds of the invention may be administered to a human patient or to a non-human mammal patient, such as horse, dog, cat etc in a continuous treatment as well as on-demand treatment, depending on the individual requirements and disease.

Pharmaceutical Compositions

In yet a further aspect, the invention relates to pharmaceutical compositions comprising the substituted imidazo[1,2-a]pyridines of the invention, or pharmaceutically acceptable salts thereof, as active ingredients.

For therapeutic use, the compounds of the invention are formulated into pharmaceutical compositions for oral, rectal, parenteral or other mode of administration. The pharmaceutical compositions contain the substance of the invention in combination with one or more pharmaceutically acceptable ingredients/excipients. The pharmaceutical compositions may comprise a carrier in the form of a solid, semi-solid or liquid diluent, or the pharmaceutical composition may be contained in a capsule.

These pharmaceutical preparations are a further object of the invention. Typically the amount of the compound of the invention in the pharmaceutical composition is between 0.1 and 90% by weight, preferably between 0.1 and −20% by weight in preparations for oral administration.

The preparation of the pharmaceutical compositions according to the invention, in the form of dosage units for oral administration, comprises the steps where the compound according to the invention is mixed with solid, powdered ingredients known in the art, such as lactose, saccharose, sorbitol, mannitol, starch, amylopectin, cellulose derivatives, gelatine, or another suitable ingredient, as well as with disintegrating agents and lubricating agents such as magnesium stearate, calcium stearate, sodium stearyl fumarate and polyethylene glycol waxes. The mixture is then processed into granules or pressed into tablets using any suitable method known in the art.

Soft gelatine capsules may be prepared with capsules containing the compounds of the invention, vegetable oil, fat or other suitable vehicle for soft gelatine capsules. Hard gelatine capsules may contain granules of the compounds of the invention. Hard gelatine capsules may also contain compounds of the invention in combination with solid powdered ingredients such as lactose, saccharose, sorbitol, mannitol, potato starch, cornstarch, amylopectin, cellulose derivatives or gelatine.

Dosage form units for rectal administration may be prepared (i) in the form of suppositories, which contain the compounds of the invention mixed with a neutral fat base; (ii) in the form of a gelatine rectal capsule, which contains the compounds of the invention in a mixture with a vegetable oil, paraffin oil or other suitable vehicle for gelatine rectal capsules; (iii) in the form of a ready-made micro-enema; or (iv) in the form of a dry micro-enema formulation to be reconstituted in a suitable solvent just prior to administration.

Liquid preparations for oral administration may be prepared in the form of syrups or suspensions, e.g. solutions or suspensions containing from 0.1% to 20% by weight of the compound of the invention and the remainder consisting of sugar or sugar alcohols and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of dry powder to be reconstituted with a suitable solvent prior to use.

Solutions for parenteral administration may be prepared as a solution of the compounds of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The compounds according to the invention may also be used in formulations together with other active ingredients, e.g. for the treatment or prophylaxis of conditions involving infection by *Helicobacter pylori* of human gastric mucosa. Such other active ingredients may be antimicrobial agents and in particular:

B-lactam antibiotics such as amoxicillin, ampicillin, cephalothin, cefaclor or cefixime;
macrolides such as erythromycin or clarithromycin;
aminoglycosides such as gentamycin, kanamycin or amikacin;
quinolones such as norfloxacin, ciprofloxacin or enoxacin;
others, such as metronidazole, nitrofurantoin or chloramphenicol; or
preparations containing bismuth salts such as bismuth subcitrate, bismuth subsalicylate, bismuth subcarbonat, bismuth subnitrate or bismuth subgallate.

The compounds according to the invention may also be used together or in combination for simultaneous, separate or sequential use with antacids such as aluminium hydroxide, magnesium carbonate and magnesium hydroxide or alginic acid, or together or in combination for simultaneous, separate or sequential use with pharmaceuticals which inhibit acid secretion, such as H2-blockers (e.g. cimetidine, ranitidine), H+K+-ATPase inhibitors (e.g. omeprazole, pantoprazole, lansoprazole, rabeprazole or tenatoprazole), or together or in combination for simultaneous, separate or sequential use with gastroprokinetics (e.g. cisapride or mosapride).

The compounds according to the invention may also be used together or in combination for simultaneous, separate or sequential use with other active ingredients, e.g. for the treatment or prophylaxis of conditions involving medicament induced gastric ulcer. Such other active ingredients may be a NSAID, a NO-releasing NSAID, a COX-2-inhibitor or a bisphosphonate.

The compounds according to the invention may also be used together or in combination for simultaneous, separate or sequential use with a gastrin antagonist such as CCK2 antagonist.

The compounds according to the invention are suitably used in a method of treatment and/or prevention of gastric acid related diseases, gastrointestinal inflammatory diseases, heartburn, symptomatic GERD, erosive esophagitis, peptic ulcer disease, regurgitation, acid reflux diseases or nausea in human or non-human mammal, comprising administering an effective amount of a compound according to the invention to a human or non-human mammal in need thereof.

The invention is illustrated in more detail with the following examples, however it is evident to man skilled in the art that the scope of the invention is not meant to be limited to the examples only.

EXAMPLES

Example 1

Preparation of 5-{2-[({8-[(2,6-dimethylbenzyl)amino]-2,3-dimethylimidazo[1,2-a]pyridin-6-yl}carbonyl)amino]ethoxy}-5-oxopentanoic Acid

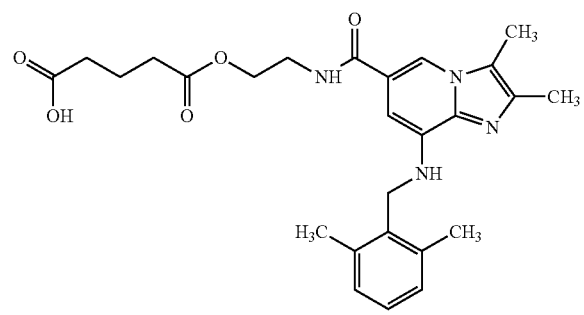 [SMILES: Cc1cccc(C)c1CNc1cc(C(=O)NCCOC(=O)CCCC(=O)O)cn2c(C)c(C)nc12]

2,3-dimethyl-8-(2,6-dimethylbenzylamino)-N-hydroxyethyl-imidazo[1,2-a]pyridine-6-carboxamide (obtained using the process according to WO02/20523) (2.0 g, 5.46 mmol) and glutaric anhydride (0.95 g, 8.33 mmol) was added to DMF (10 ml). The mixture was heated to 80° C. and stirred 16 h at this temperature. Acetone (20 ml) was added to the reaction mixture whereby the product started to crystallize. The mixture was cooled to room temperature. After 4 h the product was filtered off and washed with acetone (20 ml). 2.25 g (86%) of the title compound was obtained. The structure of the compound was confirmed with $^1$H-NMR spectrum.

$^1$H-NMR (300 MHz, DMSO): δ 1.73 (m, 2H), 2.2-2.4 (m, 16H), 3.52 (m, 2H), 4.18 (t, 2H), 4.36 (d, 2H), 4.99 (t, 1H), 6.67 (s, 1H), 7.0-7.2 (m, 3H), 8.04 (s, 1H), 8.56 (t, 1H), 12.10 (bs, 1H).

Example 2

Preparation of 4-{2-[({8-[(2,6-dimethylbenzyl)amino]-2,3-dimethylimidazo[1,2-a]pyridin-6-yl}carbonyl)amino]ethoxy}-4-oxobutanoic Acid

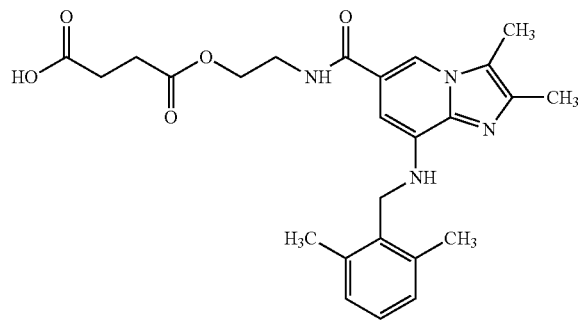 [SMILES: Cc1cccc(C)c1CNc1cc(C(=O)NCCOC(=O)CCC(=O)O)cn2c(C)c(C)nc12]

2,3-dimethyl-8-(2,6-dimethylbenzylamino)-N-hydroxyethyl-imidazo[1,2-a]pyridine-6-carboxamide (obtained using the process according to WO2/20523) (250 mg, 0.680 mmol) and succinic anhydride (150 mg, 1.50 mmol) was added to DMF (2 ml). The mixture was stirred for 16 h at 70° C. Acetone (7 ml) was added and the mixture was cooled to room temperature. After a few hours stirring at room temperature the formed precipitate was filtered off and washed with acetone (10 ml). 280 mg (88%) of the title compound was obtained. The structure of the compound was confirmed with $^1$H-NMR spectrum.

$^1$H-NMR (300 MHz, DMSO): δ 2.22 (s, 3H), 2.33 (s, 6H), 2.37 (s, 3H), 2.45-2.50 (m, 4H), 3.51 (m, 2H), 4.16 (t, 2H), 4.36 (d, 2H), 4.99 (t, 1H), 6.67 (s, 1H), 7.0-7.2 (m, 3H), 8.04 (s, 1H), 3.55 (t, 1H), 12.21 (s, 1H).

Example 3

Preparation of Starting Material 2,3-dimethyl-8-(2,6-dimethylbenzylamino)-N-hydroxyethyl-imidazo[1,2-a]pyridine-6-carboxamide Isopropyl 8-[(2,6-dimethylbenzyl)amino]-2.3-dimethylimidazo[1,2-a]pyridine-6-carboxylate (obtained as described in WO2/20523) (5 g, 14 mmol), ethanolamine (2.0 g 33 mmol) and 1,8-diazabicyclo(5.4.0)undec-7-ene (DBU) 1.5 g, 10 mmol) were dissolved in methanol (25 ml). The mixture was refluxed over night. The reaction mixture was cooled to 5° C. The solid product was filtered off and washed with methanol (15 ml). 4.2 g (84%) of the title compound was obtained as a white solid. The structure of the compound was confirmed with $^1$H-NMR spectrum.

$^1$H-NMR (300 MHz, DMSO): δ 2.23 (s, 3H), 2.34 (s, 6H), 2.37 (s, 2H), 3.3-3.4 (m, 2H), 3.5-3.6 (m, 2H), 4.37 (d, 2H), 4.77 (t, 1H), 4.97 (t, 1H), 6.71 (s, 1H), 7.0-7.2 (m, 3H), 8.08 (s, 1H), 8.44 (t, 1H).

Biological Effect

Biological tests of the compounds according to the invention in order to confirm the biological effect of the compounds were carried out as in vivo experiments.

Inhibiting Effect on Acid Secretion in Female Rats

Female rats of the Sprague-Dawley strain were used. They were equipped with cannulated fistulae in the stomach (lumen) and the upper part of the duodenum, for collection of gastric secretions and administration of test substances, respectively. A recovery period of 14 days after surgery was allowed before testing commenced.

Before secretory tests, the animals were deprived of food but not water for 20 h. The stomach was repeatedly washed through the gastric cannula with tap water (+37° C.), and 6 ml Ringer-Glucose given subcutaneously. Acid secretion was stimulated with infusion during 2.5-4 h (1.2 ml/h, subcutaneously) of pentagastrin and carbachol (20 and 110 nmol/kg·h, respectively), during which time gastric secretions were collected in 30-min fractions. Test substance or vehicle were given either at 60 min after starting the stimulation (intravenous and intraduodenal dosing, 1 ml/kg), or 2 h before starting the stimulation (oral dosing, 5 ml/kg, gastric cannula closed). The time interval between dosing and stimulation may be increased in order to study the duration of action. Gastric juice samples were titrated to pH 7.0 with NaOH, 0.1M, and acid output calculated as the product of titrant volume and concentration.

Further calculations were based on group mean responses from 4-6 rats. In the case of administration during stimulation, the acid output during the periods after administration of test substance or vehicle were expressed as fractional responses, setting the acid output in the 30-min period preceding administration to 1.0. Percentage inhibition was calculated from the fractional responses elicited by test compound and vehicle. In the case of administration before stimulation, percentage inhibition was calculated directly from acid output recorded after test compound and vehicle. Pentagastrin stimulated acid secretion was inhibited in the rat with both compounds of the invention with more than 70% after administration of 1 μmol/kg per orally.

The invention claimed is:

1. A substituted imidazo[1,2-a]pyridine of formula I or a pharmaceutically acceptable salt thereof

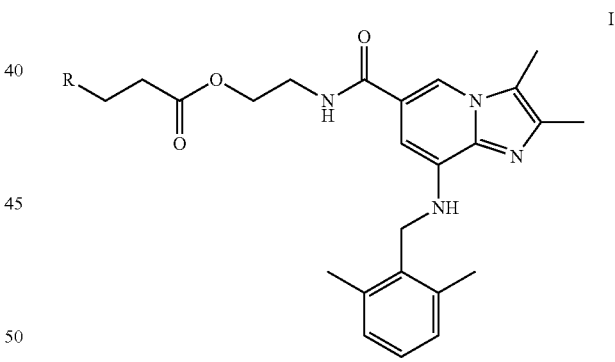

where R is —CH$_2$COOH or —COOH.

2. The substituted imidazo[1,2-a]pyridine according to claim 1, wherein the compound of formula I is 5-{2-[({8-[(2,6-dimethylbenzyl)amino]-2,3-dimethylimidazo[1,2-a]pyridin-6-yl}carbonyl)-amino]ethoxy}-5-oxopentanoic acid or a pharmaceutically acceptable salt thereof.

3. The substituted imidazo[1,2-a]pyridine according to claim 1, wherein the compound of formula I is 4-{2-[({8-[(2,6-dimethylbenzyl)amino]-2,3-dimethylimidazo[1,2-a]pyridin-6-yl}carbonyl)-amino]ethoxy}-4-oxobutanoic acid or a pharmaceutically acceptable salt thereof.

4. The substituted imidazo[1,2-a]pyridine according to claim 1, form by reacting 2,3-dimethyl-8-(2,6-dimethylbenzylamino)-N-hydroxyethyl-imidazo[1,2-a]pyridine-6-carboxamide of formula II

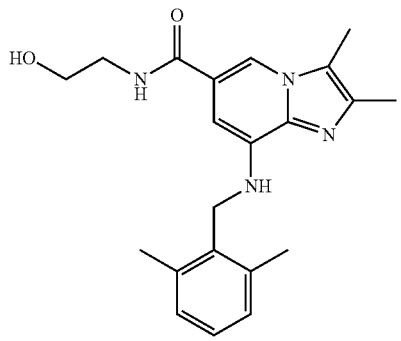

with an anhydride selected from glutaric anhydride and/or succinic anhydride in a solvent at a temperature ranging from 40 to 130° C.

5. The substituted imidazo[1,2-a]pyridine according to claim 4, wherein the solvent is selected from the group consisting of dimethylformamide, dimethylacetamide, N-methylpyrrolidone, tetrahydrofurane, cyclic ketones and alicyclic ketones.

6. The substituted imidazo[1,2-a]pyridine according to claim 4, wherein the process is carried out under a pressure ranging from atmospheric pressure to $5 \times 10^2$ Kpa.

7. The substituted imidazo[1,2-a]pyridine according to claim 1 wherein the substituted imidazo[1,2-a]pyridine of formula I or a pharmaceutically acceptable salt thereof

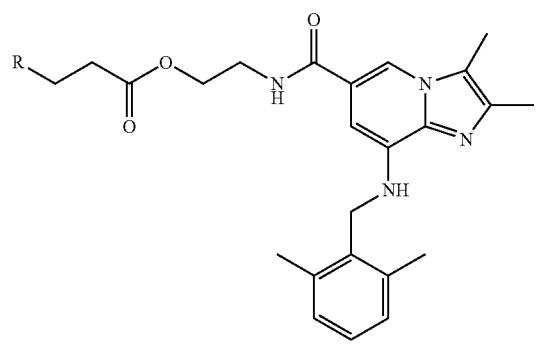

where R is —CH$_2$COOH or —COOH is in combination with a pharmaceutically acceptable diluent or carrier.

8. A process for preparation of a substituted imidazo[1,2-a]pyridine including the following steps:

a) providing 2,3-dimethyl-8-(2,6-dimethylbenzylamino)-N-hydroxyethyl-imidazo[1,2-a]pyridine-6-carboxamide of formula III:

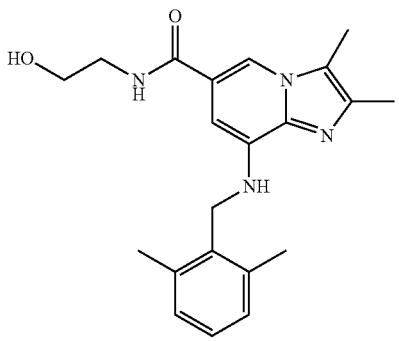

b) reacting step a) with an anhydride selected from glutaric anhydride and/or succinic anhydride in a solvent at a temperature ranging from 40 to 130° C., wherein a final product is a substituted imidazo[1,2-a]pyridine of formula IV or a pharmaceutically acceptable salt thereof

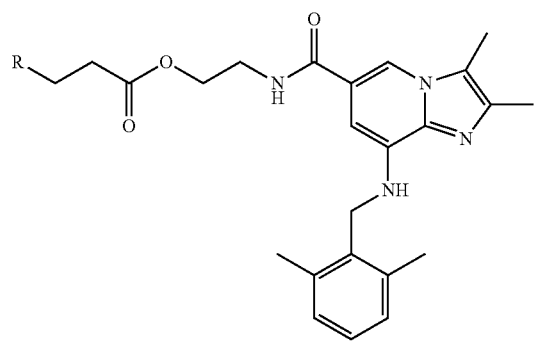

where R is —CH$_2$COOH or —COOH.

9. The process according to claim 8, wherein the solvent is selected from the group consisting of dimethylformamide, dimethylacetamide, N-methylpyrrolidone, tetrahydrofurane, cyclic ketones and alicyclic ketones.

10. The process according to claim 9, wherein the process is carried out under a pressure ranging from atmospheric pressure to $5 \times 10^2$ Kpa.

* * * * *